United States Patent
Lauer

(10) Patent No.: US 10,357,644 B2
(45) Date of Patent: Jul. 23, 2019

(54) PRESTRESSED VALVE FOR A MEDICAL FUNCTIONAL DEVICE AND A MEDICAL FUNCTIONAL DEVICE

(71) Applicant: FRESENIUS MEDICAL CARE DEUTSCHLAND GMBH, Bad Homburg (DE)

(72) Inventor: Martin Lauer, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 163 days.

(21) Appl. No.: 15/126,238

(22) PCT Filed: Mar. 13, 2015

(86) PCT No.: PCT/EP2015/055321
§ 371 (c)(1),
(2) Date: Sep. 14, 2016

(87) PCT Pub. No.: WO2015/136084
PCT Pub. Date: Sep. 17, 2015

(65) Prior Publication Data
US 2017/0080204 A1 Mar. 23, 2017

(30) Foreign Application Priority Data
Mar. 14, 2014 (DE) .................. 10 2014 103 508

(51) Int. Cl.
*A61M 37/00* (2006.01)
*A61M 39/24* (2006.01)
(Continued)

(52) U.S. Cl.
CPC ............ *A61M 39/24* (2013.01); *A61M 39/20* (2013.01); *A61M 2039/226* (2013.01); *A61M 2039/2433* (2013.01); *A61M 2205/128* (2013.01)

(58) Field of Classification Search
CPC .................. A61M 39/24; A61M 39/20; A61M 2039/2433; A61M 2039/226; A61M 2205/128; F16K 15/141
See application file for complete search history.

(56) References Cited

U.S. PATENT DOCUMENTS 3,985,141 A * 10/1976 Stanley ............... A61M 16/044
128/207.15
4,819,684 A 4/1989 Zaugg et al.
(Continued)

FOREIGN PATENT DOCUMENTS

DE 10 2099 024469 A1 1/2011
EP 2 433 550 A1 3/2012
(Continued)

OTHER PUBLICATIONS

English translation of description of Lauer (DE 102009024469).*
International Search Report from PCT/EP2015/055321, dated May 13, 2015.

*Primary Examiner* — Ariana Zimbouski
(74) *Attorney, Agent, or Firm* — Fish & Richardson P.C.

(57) ABSTRACT

A valve arrangement for a medical functional device, wherein the valve arrangement comprises a valve body, which is connected with a separately thereof produced or manufactured cap, wherein the valve body comprises at least one element or spring element, which effects a prestressing or bias of the valve body in the cap.

18 Claims, 6 Drawing Sheets

(51) Int. Cl.
*A61M 39/20* (2006.01)
*A61M 39/22* (2006.01)

(56) References Cited

U.S. PATENT DOCUMENTS

| | | | | |
|---|---|---|---|---|
| 4,946,448 | A * | 8/1990 | Richmond | A61M 39/24 |
| | | | | 137/493.9 |
| 5,228,646 | A | 7/1993 | Raines | |
| 5,992,462 | A * | 11/1999 | Atkinson | A61M 39/24 |
| | | | | 137/515.5 |
| 9,775,980 | B2 * | 10/2017 | Macy, Jr. | A61M 39/26 |
| 2002/0062109 | A1 | 5/2002 | Lauer | |
| 2006/0022464 | A1 * | 2/2006 | Lambert | A61M 16/08 |
| | | | | 285/376 |
| 2008/0161758 | A1 | 7/2008 | Insignares | |
| 2010/0198155 | A1 * | 8/2010 | Moy | A61M 5/16886 |
| | | | | 604/118 |
| 2010/0274169 | A1 | 10/2010 | Lauer | |
| 2011/0015610 | A1 * | 1/2011 | Plahey | A61M 1/28 |
| | | | | 604/500 |
| 2012/0181231 | A1 * | 7/2012 | Beden | A61M 1/1037 |
| | | | | 210/646 |
| 2013/0030342 | A1 * | 1/2013 | Scheremet | A61F 13/143 |
| | | | | 602/48 |
| 2014/0263319 | A1 * | 9/2014 | Fazi | B65D 77/0486 |
| | | | | 220/230 |

FOREIGN PATENT DOCUMENTS

| | | |
|---|---|---|
| JP | 2002-177383 | 6/2002 |
| WO | 2011-095766 A1 | 8/2011 |
| WO | 2012-049262 A2 | 4/2012 |
| WO | 2013-061876 A1 | 5/2013 |

* cited by examiner

PRESTRESSED VALVE FOR A MEDICAL FUNCTIONAL DEVICE AND A MEDICAL FUNCTIONAL DEVICE

CROSS REFERENCE TO RELATED APPLICATIONS

The present application is the national stage entry of International Patent Application No. PCT/EP2015/055321, filed on Mar. 13, 2015, and claims priority to Application No. DE 10 2014 103 508.9, filed in the Federal Republic of Germany on Mar. 14, 2014, the disclosures of which are expressly incorporated herein in its entirety by reference thereto.

FIELD OF THE INVENTION

The present invention relates to a valve arrangement for a medical functional device, wherein the valve arrangement comprises a valve body, which is connected to a cap, and wherein the valve body comprises at least one element or spring element, which effects a prestressing or bias of the valve body or at least one section of the valve body in the cap, and a medical functional device comprising a valve seat and such a valve arrangement received therein.

BACKGROUND

Single-use systems are being increasingly realized in the medical or laboratory technology as compact medical functional devices such as cassette systems or blood treatment cassettes in which liquids and gases, in particular medical fluids and blood, are conducted in channels and chambers.

Valves are used in those cassette systems, however also as a single arrangement inserted into tubes to lock the flow of fluids actively or passively, i.e. without the presence of actively driven or powered valves, in the desired counter-flow direction and to release it in the desired direction of flow, often only starting from a certain opening pressure.

The object of the present invention is to propose a further valve for a medical functional device and a further medical functional device having at least one such valve (herein also denoted as valve arrangement).

The object of the present invention may be solved by a valve arrangement and by a medical functional device according to the invention.

SUMMARY

According to the present invention, a valve arrangement is therefore proposed, wherein the valve arrangement comprises a valve body. The valve body is connected with a separately thereof produced or manufactured cap. The valve body comprises at least one element or spring element, which effects the prestressing or bias of the valve body or at least one section thereof in the cap.

According to the present invention a medical functional device is further proposed having a valve seat in which a valve arrangement is received according to the present invention.

In all of the following embodiments, the use of the expressions "may be" or "may have" etc., is to be understood synonymously with "preferably is" or "preferably has" etc., respectively, and is intended to illustrate an exemplary embodiment according to the present invention.

Whenever a numerical word is mentioned herein, the skilled person understands this as an indication of a numerical lower limit. Provided it does not lead to any contradiction discernible for the skilled person, the skilled person in these cases implicitly understands for example "one" always as "at least one". This understanding is also encompassed by the present invention as well as the interpretation that a numeric word, for example, "one" can alternatively be meant as "exactly one", wherever this is technically possible in the view of the skilled person. Both are encompassed by the present invention and apply to all used numerical words herein.

Advantageous developments of the present invention are the subject-matter of dependent claims and embodiments respectively.

Embodiments according to the present invention may comprise one or more of the following features in any arbitrary combination.

In the following, there shall be a repeated mentioning of a first position and a second position. Hereby, it may refer to any positions or valve positions, which may comprise or take the valve arrangement according to the present invention (e.g. open and closed, or half-open and completely open).

In all of the embodiments according to the present invention, the cap may be embodied as snap-in cap. The expressions "cap" and "snap-in cap" may be interchanged.

In some embodiments according to present invention, the first position describes a position for ensuring the gas sterilizability, also denoted as a primarily, flow-open "initial" position. In certain embodiments according to the present invention, the valve arrangement according to the present invention, especially when the valve arrangement is designed as a check valve, may be transferred out of the initial position, when the blood treatment apparatus is equipped with the functional device, into the second position, the so-called "activated" position. Only at the point of this transfer, denoted here as "activation", the valve, when designed as a check valve, has the function of non-return; not already beforehand.

In some particular exemplary embodiments of the functional device according to the present invention, the actuation of the valve is generally achieved through impression of a path/a movement or shift. The herein indicated force is thus a reaction thereto.

In some exemplary embodiments of the medical functional device according to the present invention, the valve is embodied to be actuated or operated by means of an actuator of a blood treatment apparatus. Thereby, the functional device is connected, for its operation, with the blood treatment apparatus.

In certain exemplary embodiments of the present invention, a prestressing or bias is to be understood as stress or tension or warping or rigging of the element or of the spring element, which is there already prior to engaging the cap together with the valve body, being engaged in the cap, at least one of in the valve seat or prior to first actuating the valve through, e.g., an actuator of a blood treatment apparatus.

In some exemplary embodiments of the valve arrangement according to the present invention, the valve arrangement and the valve seat are embodied or aligned or coordinated with each other such that the prestressing or bias, through actuating or moving or shifting at least one of the cap or the valve body within the valve seat, is transferred into a stress, replaced by it or overlapped or overlaid through it.

The stress may, for example, be effected or initiated by an actuator of a blood treatment apparatus.

The prestressing or bias may be effected in that the valve body, by means of exactly two or at least two sections—which are in connection, preferably in a flux-of-force connection with the spring element—touches or contacts the cap, is in contact with it or comprises it in order to achieve the prestressing or bias. Both of these sections are, for example, ring front/end and tension rod of the valve body, support flange and conical mandrel or pin or support ring and front/end surface of the centering cone.

The stress, which may replace or overlap or overlay the prestressing or bias, may effect that at least one of the respective two previously mentioned pairs of the sections of the valve body—e.g. the tension rod, the support flange or the support ring—by means of which the prestressing or bias has been achieved, quits or ceases the contact to the cap.

In specific embodiments according to the present invention, the valve body is supported at the valve seat after the contact has stopped, either as a replacement or instead of the ceased contact, as described above.

In some embodiments of the functional device according to the present invention, the valve body, when the actuator acts on or effects the cap, undergoes a higher warping or tensioning than through the prestressing or bias alone. In specific embodiments of said embodiments, the valve body is stressed, through the arising of stress, further in the same direction as through the prestressing or bias alone. Therefore, in some of these embodiments, stress further increases the warping or tensioning, which is achieved through prestressing or bias.

In some particular embodiments of the functional device according to the present invention, the element or spring element is substantially or solely a part of a section of the valve body.

In certain exemplary embodiments according to the present invention, the element or spring element is a one-piece or an integral component of the valve body.

In specific embodiments of the functional device according to the present invention, the element or spring element is prestressed or tensed in exactly one or at least one position of the valve, in other embodiments according to the present invention, it is prestressed or tensed in all positions, in particular, in all mounting or usage positions.

In some exemplary embodiments of the functional device according to the present invention, the valve comprises, or is, at least one of the valve body or the cap or snap-in cap; in these embodiments, the valve seat is not part of the valve. Whereas, in other exemplary embodiments according to the present invention the valve seat is also part of the valve.

In certain exemplary embodiments according to the present invention, the functional device is embodied such that the cap, where available, does not move relative to the valve seat when the valve is being opened.

In some particular exemplary embodiments according to the present invention, the valve body comprises a number of knobs. They radially extend out of the openings or through-openings of the cap, after the connection of the valve body with the cap.

In certain exemplary embodiments according to the present invention, both the valve body and the cap comprise drainage structures.

In some exemplary embodiments of the functional device according to the present invention, a step or layer or a step-like diameter restriction is embodied within the cylinder-shaped section of the valve seat of the cassette in the support ring area.

In some particular exemplary embodiments of the functional device according to the present invention, at least one of the valve seat or the sealing section present in the sealing area are designed conically or flat. At least one of the valve body or the cap seal against the sealing area in at least one position of the valve.

In certain exemplary embodiments of the functional device according to the present invention, the valve body is radially positioned in the cap under a first prestressing or bias and axially under a second prestressing or bias. Hereby, the second prestressing or bias may be larger the first one.

In some exemplary embodiments of the functional device according to the present invention, the valve body has the form of a cup with a valve tray and optionally has a centrally, and exemplary, stiffly-fastened tension rod at the valve tray. Thereby, the tension rod is designed for connecting the valve body with the cap in that the tension rod is snapped-in or engaged in a snap-in opening of the cap or snap-in cap.

In some particular exemplary embodiments of the functional device according to the present invention, the cap comprises tongues or pins which extend radially.

In certain exemplary embodiments of the functional device according to the present invention, the tension rod and a valve tray are sufficiently stiff such that the tension rod in the cap maintains in at least one position, e.g. the second position, in all spatial directions, a contact-free distance to further or to all positions.

In some particular exemplary embodiments of the functional device according to the present invention, the cap has the form of an arch having several openings or through-openings which are radially to the outside and axially at the top open. Further, snap-in tongues or pins are arranged in the through-openings, which only partially cover the openings or through openings when they are radially inwardly bent.

In certain exemplary embodiments of the functional device according to the present invention, the number of openings or through-openings and the snap-in tongues or pins is uneven, respectively.

In some particular exemplary embodiments according to the present invention, the valve is embodied such that the valve body is snapped-in or locked in place, jammed, wedged or the like in the cap. Thereby, the valve body may deform elastically. In certain embodiments according to the present invention, it is thereby a support ring of the valve body which snaps in, jams, wedges or the like behind or beneath sections of the cap, such as the optional support tongues or pins of the cap, while a further section of the valve body, such as an optional centering cone thereof, presses under effect of a spring element against an again further section of the cap, such as an optional cone reception.

The spring element in certain exemplary embodiments of the functional device according to the present invention, is designed as an elastical section, preferably of the valve body. The spring element may be a spring membrane. The spring membrane may be closed or peripheral or rotationally symmetric. The spring membrane may have, in a cut or cross section, a cup-shaped section. The spring membrane may comprise in a cut or cross section concentric sections.

In some exemplary embodiments of the functional device according to the present invention, the prestress is effected by means of a spring element which is exemplary a spring membrane.

In some particular exemplary embodiments of the functional device according to the present invention, the spring element is a section of the valve body.

In some exemplary embodiments of the functional device according to the present invention, the cap comprises a closed or peripheral edge. The latter is located at the level of the snap-in tongue or pin and forms thereby the main separation plane of the injection molding. The closed or peripheral edge may in certain exemplary embodiments according to the present invention effect or cause a deviation of the cap from the cylinder form which may advantageously prevent a canting or jamming of the cap when it is tilted or when subject to tilting movements.

In some particular exemplary embodiments of the functional device according to the present invention, a closed or peripheral slot or split, denoted herein as sterilization slot, remains in the first position. This axial mounting position and therewith the sterilization slot or split are held up or maintained in the form of clamping centering ribs as an example of a friction closure element, through friction closure of components contacting each other, preferably a valve seat on the one end and a valve body on the other end. The sterilization slot may be flowed through by sterilization fluid in the open position. It is preferably closed in the closed position or does not exist anymore.

In certain exemplary embodiments according to the present invention, the functional device is designed as a blood cassette, a cassette, a blood tube or an infusion tube.

In some exemplary embodiments according to the present invention, the functional device is designed as a blood cassette which comprises a hard body and a film covering the hard body or parts thereof. Thereby, the valve seat is provided in the hard body. The valve is arranged to be actuated or operated or moved or shifted by means of pressure or moving or shifting of an actuator of the blood treatment apparatus on the film.

In certain exemplary embodiments according to the present invention, the valve arrangement is embodied to be closed by means of an actuator of a blood treatment apparatus.

In some exemplary embodiments according to the present invention, the valve arrangement is embodied to be used as a check valve.

In some particular exemplary embodiments of the functional device according to the present invention, the film-sided front/end surface of the valve does not protrude beyond the film plane of the blood cassette.

In certain embodiments according to the present invention, a one-piece valve body is made up of silicon rubber. The valve body may comprise a preferably cup-shaped radial sealing bar, which is fastened to a corn cylinder in a closed or peripheral fluid-tight manner.

In certain embodiments according to the present invention, the valve body comprises guiding clamping drainage ribs, which serve for guiding, clamping and draining. They are preferably fastened to the corn cylinder in an equal and odd-numbered division and in a preferred number of more than 2.

The valve seat may in certain embodiments according to the present invention comprise two adjacent cylinders, here, being a guiding cylinder (down in the valve seat) and a sealing cylinder (at the top in the valve seat), wherein the sealing cylinder has a larger diameter than the guiding cylinder, and wherein the area of the diameter transition or stage or step between both cylinders is denoted as snap-in transition or step. At least some of the clamping guiding knobs of the valve body or the guiding clamping drainage ribs are positioned in one or in the first position at the guiding cylinder. The clamping snap-in knobs which protrude beyond the aforementioned clamping guiding knobs are positioned in the first position at the sealing cylinder. Both clamping snap-in knobs and the aforementioned clamping guiding knobs are positioned at the guiding cylinder in a second position.

In certain embodiments according to the present invention, a radial sealing bar of the valve body is not axially meshed to the sealing cylinder, therefore there is a fluid-open ring volume (a sterilization slot). Only by operational discharge of an axial minimum activation force (preferred is 20 to 40 N) onto the front/end surface of the core cylinder, a shifting movement is introduced.

Drainage bottom ribs are located in certain embodiments according to the present invention, in the second position, at a lower section, e.g. the bottom, of the guiding cylinder. They may hereby limit the activation hub and ensure, together with all the other ribs, the equal de-aeration and circulation properties of the valve body as well as the safe sterilizability by means of gases.

In certain embodiments according to the present invention, the closed or peripheral radial sealing bar, preferably having a pointed sealing edge, forms together with the sealing cylinder of the valve seat of the cassette a check valve sealing system, and that after an activation hub has been executed. Thereby, the closed sealing edge of the valve body—preferably made from elastomer—abuts on the sealing cylinder under radial prestressing or bias.

In certain embodiments according to the present invention, the valve body consists of an elastomer material, preferably of silicon rubber.

In certain embodiments according to the present invention, the positioning ring of the valve body comprises several drainage structures, preferably peripherally arranged, which ensure in the mounted state the accessibility for the sterilizing gases.

In certain embodiments according to the present invention, the upper ring front/end surface of the positioning ring sits flush or leveled with the film or the cassette edge at or on which the film is hung up or welded.

In certain embodiments according to the present invention, an outer envelope surface of the positioning ring comprises a larger diameter than the landing or change bore attached thereto in the cassette. Through the diameter difference, at least one of the hardness of the material or the design of the drainage structures, a retention force caused by friction may arise.

In certain embodiments according to the present invention, a lower ring front/end surface of the positioning ring serves as movement stop and therewith the calibration of the opening pressure and the outlet characteristic for the valve.

In certain embodiments according to the present invention, an outlet ring zone consists of single, spiral, loop-shaped single bars having slots in between. It serves for the fluid outlet, e.g. into the second position, holds the valve core in the set position and builds an axially springy and tilting-position-compensating support structures.

In certain embodiments according to the present invention, the valve body comprises a preferably mushroom-shaped valve core. The latter comprises a preferably stiffer core area which acts as movement limitation in both axial movement directions, i.e. at its upper side against the film and at its lower side against a cassette-sided plunger.

The stoppers are touched only when the specified pressure and volume flow area is left. A sealing ring zone of the valve comprises in a first position a ring slot—of e.g. ca. 0.4 mm—for the safe gas sterilization. In a second position, it seals, preferably under minimum prestressing or bias of ca. 0.4 mm, against, for example a conical or flat, sealing seat of the valve seat.

In certain embodiments according to the present invention, the cap is preferably made from thermoplastic, preferably, polypropylene (in short: PP).

In certain embodiments according to the present invention, the valve body having a sealing ring comprises a number of knobs which radially outwardly project out of through openings of the cap after the pre-assembly of the valve body with the cap.

In certain embodiments according to the present invention, a step (step-like diameter restriction) denoted as diameter landing or change is provided within the cylinder-shaped section of the valve seat of the cassette in the support ring area. It is possible to use the valve as a check valve when the knobs, radially protruding beyond the diameter landing, are shifted into the valve seat of the cassette or when a ring front/end surface of the cap comes closer to the ring front/end surface of the valve seat until a surface contact between them has been reached.

In certain embodiments according to the present invention, the cap is stiffer in comparison with the valve body.

In certain embodiments according to the present invention, the valve arrangement according to the present invention may be two-piece.

In certain embodiments according to the present invention, the valve arrangement may seal in a flat manner. "Flat" means in specific embodiments according to the present invention that the sealing area is, preferably completely, substantially or partially at least one of plane or parallel to a film plane. The sealing area, in some particular embodiments according to the present invention, may preferably completely or substantially be positioned in a plane which is perpendicular to the shifting direction of the valve body.

In certain embodiments according to the present invention, the valve seat against which at least one of the valve body or the cap seals in the second position, is embodied, in the sealing area, conically or, in cut or cross-section, cone-shaped.

In certain embodiments according to the present invention, the valve body has the shape of a cup with a bellows-type envelope, an optional largely flat, stiffly-designed valve body and an optional tension rod, which is centrally and stiffly attached to the valve tray. The tension rod is designed for the connection between valve body and cap, e.g., in that the tension rod is snapped in or engaged in a suitable central snap-in opening of the cap.

The ring front/end of the bellows envelope facing away from the valve body is positioned in certain embodiments according to the present invention radially, under, preferably, lighter prestressing or bias and axially under larger prestressing or bias than radially in the cap. Thereby, the bellows envelope is correspondingly compressed and the axial prestressing or bias on the snapped-in tension rod is maintained. This axial prestressing or bias may be denoted herein as prestressing or bias of the valve.

The cap, in certain embodiments according to the present invention, is made from the relatively stiff material PP (bending modulus of elasticity ca. 1750 N/mm).

The cap, in certain embodiments according to the present invention, is designed with radially springy tongues or pins.

In certain embodiments according to the present invention, the tension rod and the valve tray are embodied sufficiently stiff so that the tension rod maintains in at least one direction a contact-free distance in all spatial directions to the mounting surrounding in the cap.

In certain embodiments according to the present invention, the cap or snap-in cap (both expressions are to be understood as interchangeable provided the cap can be snapped in the respective embodiments) additionally comprises at a lower ring front/end several locking lugs which are radially inwardly abutting or protruding.

The cap, in certain embodiments according to the present invention, is designed so that it may be produced in a multiple on-off injection molding with central hot channel gatings, respectively.

The valve body comprises, in certain embodiments according to the present invention, a central conical pin, which is received in a play-free manner in a corresponding cone of the cap.

A connecting membrane or membrane extends, in certain embodiments according to the present invention, between a cone and a support sealing ring of the valve body.

In certain embodiments according to the present invention, the valve body comprises, in a non-built-in state, a slight warping, to the bottom, of its centrally-arranged connecting membrane, i.e. in an assembled state towards the valve seat of the medical functional device.

In the pre-assembly of the valve body into the cap, this curvature is, in certain embodiments according to the present invention, already neutralized through a snap-in of a support flange of the valve body until its toothing with the retaining lugs of the cap, or the connecting membrane is already so elastically deformed that a light curvature takes place in the opposite direction, hence upwardly, i.e. away from the valve seat. The curvature in an opposite direction strengthens once again, in certain embodiments according to the present invention, during or through moving or shifting the cap into the valve seat. In certain embodiments according to the present invention, the curvature is strengthened once again during or through its flow-through with treatment fluid.

In certain embodiments according to the present invention, the support sealing ring is more compact or thick-walled in relation to the connecting membrane.

The valve arrangement in certain embodiments according to the present invention has the form of a pin plate in cap.

In certain embodiments according to the present invention, the valve seat does not comprise any undercuts.

In certain embodiments according to the present invention, the cap has the form of an arch with several through openings which are radially to the outside or axially to the top open. Snap-in tongues or pins which may be bent radially outwardly are arranged in these through openings. The snap-in tongues or pins close the through openings only proportionally, e.g. to ca. 30%.

Spatial indications like "top", "bottom" and so on, refer in case of doubt to the illustrations as can be seen in the attached figures.

In certain embodiments according to the present invention, the number of the through openings and the number of the snap-in tongues or pins are preferably uneven, respectively.

In certain embodiments according to the present invention, the cap comprises a peripheral, preferably, sharp edge which is preferably positioned in both the supporting arches and the bendable snap-in tongues or pins at the same level and thereby forming the main separation plane of the injection molding.

In certain embodiments according to present invention, an upper ring front/end of a cap forms the highest section of the arch construction and represents through the film the mechanical cutting point for the leading-in of activation force, activation path and retention force by the actuator-sensor-unit of the treatment machine. It represents a flat ring front/end that is interrupted by structuring notches or chamfers.

In certain embodiments according to the present invention, the cap comprises at both the upper ring front/end and in the area of the cone reception numerous structurings like structuring notches or chamfers, grooves and recesses.

In order for a part to maintain a symmetrical—and by the cooling of the thermoplastic during the production—warping or deformation-unremarkable form, the outer and inner structurings are, in certain embodiments according to the present invention, arranged concentrically with the same number or with an even number divided in relation to the number of the through openings or snap-in tongue or pins.

In certain embodiments according to the present invention, the cap comprises not only the arch structure, rather also the vertical cylinder walls and conical, in particular steeply conical, peripheral walls, preferably inside and outside of a cap aligning notch.

The valve body has, or is, in certain embodiments according to the present invention, a form similar to rolling bellow and encompasses an aligning cone, stop front/end, at least two support aligning humps, a spring connecting membrane, a sealing ring and a support ring, wherein the foregoing expressions are described below, with reference to FIG. 3.

In certain embodiments according to the present invention and in order to additionally increase the insertion possibility, both the lower ring front/end of the cap and the valve seat edge are provided with curves which act as additional insertion chamfers.

In certain embodiments according to the present invention, the snap-in tongues or pins have a larger diameter of, e.g., 0.4 mm as against the outer cylinder walls of the cap.

In certain embodiments according to the present invention, the valve body is built in the cap in a pre-stressed, force-interlocking and form-interlocking and axially free-of-play manner.

Some or all embodiments according to the present invention may exhibit one or several of the aforementioned or below stated advantages.

Some valves according to the present invention may offer advantages in the automatic fabrication, the safe sterilization and the increase of the quality of the valve functions. Large-pore drainage structures to smooth films and smooth injection molding walls and a low amount of wide-area component contacts contribute thereto, low and defined changes in properties due to gas sterilization, in particular, of the opening pressure, the minimizing of changes of properties of the mounted valves caused by mechanical, thermal or irradiation-induced load during the storage and transport which may influence the process of the safe and precise activation, preventing the so-far tolerated protrusion of the film-sided front/end surface of the valves beyond the film plane of the cassette (valves cause local dents in the film) for ensuring a safe producible film welding seam based on a continuously flat film mounted onto the cassette, more-tolerant-to-tolerance design of the individual parts and their interaction by both the mounting and interaction with the treatment machine at concurrently high reproducibility of the tightness, of the pressure opening and of the discharge pressure drop curve and therethrough a safe functioning also in the high-volume production and in many or aged treatment machines available in the market, increasing the reproducibility of the discharge pressure opening, reducing the pressure drop in the discharge area, i.e. minimizing the pressure drop at each volumetric flow discharge, flattening of the curve of the volumetric flow pressure drop discharge, i.e. minimizing the increase of the pressure drop with the increase of the volumetric flow discharge, increase of the fine and long-term intrusion tightness under/below the discharge opening pressure, in particular, tightness against air intrusion, reducing the sensibility against leakage by the presence of contamination particles and improving the capability of self-cleaning, further safe and tight sealing in the exclusion area up to the maximum pressure, and preventing vibration or swinging and noise emissions.

Further advantages are:
the low risk of malfunction;
safe performance also at maximum possible axial activation hub (measured against the film) of ca. 1.2 mm, which is predetermined by the cassette construction and the blood treatment apparatus;
improving the fluidic characteristic value is achievable, as improved configuration and small tolerances in components are, in this regard, achievable;
reversible activation is feasible during the production up to the functional testing;
no problem of an uneven injection-molding production with welding lines and a thereto associated leakage;
sufficient, constant geometry after the vapor sterilization;
insignificant relaxation during the prestressed, activated position, which may reduce the valve prestressing or bias during use and in this way may have an effect on the parameter pressure opening and outflow pressure drop;
high tolerance bridging through material combination elastomer-thermoplastic and through knobs geometry, therefore a low-cost and safe production with large permissible variations or dimension tolerances;
safe axial power limitation due to being completely made from elastomer and being axially flexible through the bottom ribs;
good gas sterilizability through broad drainages and little compressing surfaces between valve body and valve seat through convexity of the clamping aligning ribs;
triggering pressure and pressure volumetric flow characteristics depend only on the selected material, the selected wall thickness and diameters and of the production tolerance of the measurements and the properties of the material, however not on the size of the activation hubs provided the effective activation hub be within the planned range (here 1.2 to 1.8 mm);
no undercuts and therewith no deformation problems by assembling the valve seat in the cassette;
simple assembly procedures;
good tolerance compensation against axial assembly tiltings;
uncoupling of the activation path, and therewith the valve prestressing or bias, of the machine tolerances;
noticeable improvement of the reproducibility of opening pressure and characteristic line of the pressure volume flow;
flattening of the characteristic line of the pressure volumetric flow which results in realizing lower pressure loss and lower opening pressure configuration;
ergonomic advantages through little injection actuating power by infusion of medication;
lower haemolysis when used for or during blood infusion;
simple preassembly of the valve in the cap or snap-in cap at higher reproducibility of the radial alignment;
possibility to test the functionality of the valve arrangement by the production after mounting of the cassette film;
due to the bellow shape of the valve, a more linear spring characteristic line is realizable as/than with, e.g., the simple mushroom shape;
the sealing ring area of the valve elements is not disposed or positioned, with regard to the flow relations in preferred production as LSR injection molding (Liquid Silicon Rubber), at the end of the flow path (such as with simple mushroom shape) and therefore avoiding weld lines and therewith the welding defects which cause leakage;

very little material and low cost are required for the manufacturing or execution of the valve (0.5 Euro cent);

easily automatable mounting of the valve arrangement in a free rotatory positioning manner;

good aligning performance of the sealing ring area;

safe avoidance of friction between valve and cap by activation and flow through;

axially, particularly, very compact valve arrangement with therewith-associated reducible flow dead spaces;

advantages in characteristics and tolerance performance like the other prestressed valve designs with cap;

gas-open initial position for ensuring safe gas sterilization performance;

robust initial position with higher release expansive force despite little activation path;

avoiding the escape of unwanted fluids, after the removal, through remanent activation;

safe remanent activation, during equipping with safe position preservation after removal through friction closure and large prestressing or bias of the activated valve;

hard enveloping cap encapsulates the soft valve against mechanical interventions or modifications;

new mechanism of snap-in tongue or pin-wedge-diameter landing for robust gas-open initial position and defined strong release expansive force;

extreme low activation path in relation to the valve diameter allows a machine-sided passive activation actuator by flat film initial position and low film stress or stressing;

new cant-safe activation or plane bearing mechanism, consciously taking into account the possible tilting in the regular shift manner;

special geometrical arrangement with reduction of the tolerance chain;

decreased tolerances through precise producible compact function-determined geometries;

reduction of the valve tolerances through mutual geometrical calibration of assembled components;

utilizing the thermal and temporal material stress reduction through sterilization and storage so that the activation expansive force is calibrated and reduced during treatment, however, it is to be set as high as possible during valve production;

uncoupling of the positioning tolerance of the valve to the valve seat from the initiated forces and paths of the treatment machine by means of interposition of the cap;

principle of prestressing or bias leads to greater prestress path and as a result the characteristics of a valve are more exact, exhibit lower pressure drop and are therefore also more taken-care-of treatment fluid (lower shear stress at same volumetric flow);

conical or spherical segment-shaped valve sealing seats lead less-tolerance valve characteristics, an increase of sealing at a non-operating step, to a capability of self-cleaning, higher sealing capability in case of impurity and material defects;

overall stiffness and local barbs and soft valve sealing ring geometry lead to higher sealing capability in case of impurity and material defects;

extremely cost-effective production of the individual component through on-off de-molding principle, minimized injection molding cycle time through equal wall thickness and less material consumption and, due to less elongation, a possible application of a film containing relatively little elastomer and therefore being cost-effective;

specifically more exact component geometry through rotationally-symmetrical stiff geometry and central gating;

no or hardly any air bubbles and weld line in the sealing ring zone through geometrical shifting away from the end of the flow path;

complete automatable production and testing concept which is conceptually included by taken into consideration all parts and handling tolerances with specially good characteristics of self-aligning and freedom of rotation positioning of all components;

complete fluidic testing of the valve in a finished, equipped state is realizable through reversible activation;

self-compensatory characteristic against relaxation in the characteristic line during use;

utilizing deformation characteristics specifically of rolling bellows for the flattening of pressure loss-volumetric flow characteristic line;

optimized drainage and sterilization patterns of the thermoplastic cap as functional improvement in comparison with patterns of the elastomer valve components;

conical alignment with a large opening angle, patterns in axial directions, matt erodings and axial support zones by the cap for optimized collaborate functionality with the soft sticky elastomer material of the valve;

possibility to set the opening pressure, because of higher reproducibility at same safety level, at a lower value, hence, more ergonomic spraying of treatment fluid, lower material-caring pressure level from supply or feeding pumps or less haemolysis by blood return through the valve;

at least one of many or uneven-numbered, equal division of through openings and snap-in tongues or pins, which enables low-pressure-drop and equal flow through of the valve arrangement, without rotary orientation also by several fluid channels going out of valve seats and having good centering property;

technically functional use of the de-molding partition line for functionalities of the vale such as friction by axial shifting and canting-insensitive tilting with omission of the usually mostly existing necessity of producing the injection molding in a burr-free manner;

extensive activation ring surface made of hard thermoplastic material reduces the activation pressing stress on the activation hump of the machine and reduces inaccuracy of the activation path transition though elastical flexibility onto machines and valve components;

advantageous form design in focus and shape symmetry of cap and valve for the safe vibration requirements and orientation sorting by provision and pre-positioning of parts;

conical, round, central geometries of cap and valve allow a suction process and precise further and end centering with tubular vacuum grabs and round reception bores;

possibility to apply or implement a specially simple and passively effective activation device on the machine side requiring neutral costs for integrating a progressively operating activation hump springing in the hermetically encapsulated actuator-sensor-mat;

possibility to apply a likewise encapsulated, inserted activation device, discretely structured with technical springs, in the area behind the actuator-sensor-mat;

possibility to apply an actively drivable activation device encapsulated behind the actuator-sensor-mat with the possibility to be able to perform a complete functionality test of the valve arrangement prior to beginning with the treatment and to further be able to procedurally use, apart from the valve function, also the function of double-sided open flow paths;

use of the differences of static friction and sliding friction in the activation mechanism of the cap in order to maintain a high activation expansive force with low further shifting force after overcoming the snap-in barrier;

use of convex or pointed knobs or shaft structures in the actuator-sensor-mat, in order to maintain a progressive force path characteristic line, which may connect a high activation expansive force with low residual force in the activated position;

valve opening occurring merely through bending processes in the elastomer valve, therefore an extensive drop of hysteresis and variations in reproducibility;

low clogging tendency through equal and complete lifting of the sealing ring when the valve in being opened while avoiding the flow dead zones and fluid dwell times at the non-lifting zones of the sealing ring;

low sensitivity to the causing of vibrations and noises or sounds, as the valve sealing ring lifts up equally and therefore substantially allowing only a basic mode of vibration.

In certain embodiments according to the present invention, the valve injection molding may advantageously be manufactured according to a low-priced on-off conception, wherein the required number of molding post, due to the longer specific cycle time for the cross linking of fluid silicones, is to be set higher up than by snap-in molding to about factor 2. It is possible to manufacture the valve in an extremely inexpensive manner through the simple and substantially rotationally symmetrical shape, through the plane, sealable, mismatch in mold and mold-parting-line-uncritical mold release at the bottom surrounding angle of the support ring and through the very small construction volume of ca. 110 mm^3. Due to the fact that LSR components are normally the ones which are swept, most economically, out of the ejector-sided mold cavity due to the lateral attached rotary spatula, the valve is therefore designed in the optimal producibility and thereby makes use of the centering cone as a central feed point and, during the de-molding process, as sweeping nipple which protrudes out of the ejector-sided mold half. The valve designs according to the present invention comprise the characteristic to be centrally molded and substantially rotationally symmetric which is advantageous for a warping or deformation-low shape of mold.

It is also advantageous that no large portion of its volume is arranged in the vicinity of the center (mushroom base area), while the portion of its volume near the sealing ring is relatively big and thereby it is not positioned in the immediate vicinity to the end of the flow path and to the mold release. The result of which is that, the liquid injection molding in the process of filling of the sealing ring area does not take place already shortly before completion of the mold filling, the flow speed does not come to a standstill and air bubbles and weld seams are not further moved. In this manner, one does not have the problem that air voids or air pockets or entrapped air and weld seams and the therewith related geometrical inaccuracy at the surface are of all things obtained at the sealing ring and therefore reducing the sealing capability of the valve at the ring-shaped area of the contact with the sealing surface at the valve seat.

The valve according to the present invention, comprises in certain embodiments according to the present invention a shape which specially supports in its production the filling of the mold form: The centrally injected liquid elastomer initially collides against the support front end and is abruptly diverted or redirected into the thin-walled wave form of the spring membrane, it flows after renewed diversion or redirection through the sealing ring and further to the relatively voluminous support ring where the mold release with the ventilation and flow path ends are positioned. The sealing ring is therefore flown in with homogenized injection molding compound by relatively high flow speed and therewith the air voids and weld seams (partially frozen or solidified flow fronts) are further moved. Hence, one obtains a sealing ring with particularly more accurate and, for sealing, more suitable surface.

Due to the low stiffness of elastomeric components (herein about 40 to 70 Shore A) and in relation to the relatively high stiffness of the cap, there are in certain embodiments according to the present invention structurings, which are advantageously arranged in the cap components rather than in the valve components, for the accessibility of sterilization gases, for the air exhaustion or outflow and friction reduction by the assembly. One needs less deep structures in the cap, in order to maintain equally large continuously-open structures in a pressed and built-up state, than by arranging corresponding structures in the valve components. This is the result of the fact that the raised and the impressed structures are flattened out at the elastomer and therefore the undesired direct surface contact between the thermoplastic and the elastomeric components increase, while at the same time, the desired gas-conducting drainage grooves decrease in cross section. In addition, it is beneficial for the error-free production of the surface of the elastomeric parts when there are no difficult-to-squeeze out and difficult-to-ventilate structures, which is not to be considered in the production of the cap due to the fact that, in this case, small defects in the surface have no influence on the function.

Further possible advantages relate in particular to the tolerance optimization. In details:

1. By the prestressing or bias of the valve in the snap-in-cap, the valve adjusts to the snap-in-cap in several axial dimensions and it orients itself towards the more rigid and more accurately producible snap-in-cap also according to the axial run-out, radial spacing and axial alignment, whereby already several dimension tolerances of the valve become less relevant or even meaningless already.
2. Due to the fact that for the position "activated", the only matter of importance is that the cap, with its lower ring front end, flatly lies at the valve seat ring support, it is meaningless which path the actuator-sensor-plate of the treatment machine takes for the shifting of the cap into the activation hump, as long as the path is at least big enough so that the cap comes to lay planar. This is a distinctive difference to most of the, softly designed, known valve designs with proportional dependence of the activation path of the valve on the activation path of the machine. One obtains an approximately complete decoupling between the activations paths of the valve and the activation actuator of the machine.
3. Due to the fact that the cap is a component which is an order of magnitude stiffer than the elastomeric valve, the axial self-deformations, under the introduced activation forces, are accordingly less. Hereby, the axial position uncertainty of the aligning cone of cap and therewith the central area of the valve drop to about more than an order of magnitude (0.02 to 0.04 mm) than with the previous designs with no cap, by which the penetration depth and axial force of the activation hump of the treatment machine had taken direct influence on the axial shifting of the central area of the valve and therewith the operational prestressing or bias of the activated valve. Thus, one obtains an approximately complete decoupling between the prestress forces of the valve in the activation position and the activation forces of the activation actuator of the machine.

4. The geometrically mechanical chain of the influencing tolerances includes only a small part of the previous dimensions, namely the dimensions of the valve and the, immediately around it, topologies of the valve seat and cap interior which are involved in the valve clamping. As all these topologies have only small dimensions in the range of 0.4 to 3.6 mm in Z-direction, the achievable production tolerances of the injection molding topologies are accordingly small and are in the range of less than +/−0.03 mm. One obtains therefore significant shortening of the tolerance chains and at the same time narrower single tolerances.

5. By the plane contact of both ring surfaces mentioned supra, under a continuous residual force of typically 5 to 20 N, the axial run-out deviations of both ring surfaces mutually reduce themselves as they mutually level themselves in an elastic-plastic manner. This is a typical process in case the axial compression injection molding components, which are basically effected by the angle deformations, are exposed against pointing counter surfaces. One obtains such an increase in accuracy by mutual design optimization of the installed components.

6. The spring membrane of the valve has a similar shape to a rolling bellows. The design-change processes by the axial deflection or modulation of the valve are not to be equated with a genuine rolling bellows, because the cylindrical rolling or turning surfaces for the prevention of movement friction are missing. The design similar to rolling bellows has specific advantages compared to a flat spring membrane:

6a. By the same axial prestressing or bias, the angle flexibility at the level of the sealing ring is clearly increased, which leads to a more even or steady sealing compression and therefore to a narrower spreading of the opening pressure by radial and angular misalignment or displacement of the symmetry axis of the valve to a symmetry axis of the valve seat.

6b. Due to the relative stiffness of the support ring in connection with the mostly vertical wall section between support ring and sealing ring, a generally-specific stiff sealing ring zone results or arises, which is shifted through the rolling membrane, rather as a whole, and thus adjusting to the sealing ring of the valve seat when shifted in an angular radial and axial manner. Locally, i.e. with reference to the local compression of the elastomeric valve sealing ring onto the hard valve seat sealing ring, the tightening adjustment of both surfaces is therefore intensified or reinforced such that the valve sealing ring builds up relative sharp edges (pointed elements of a sealing compression combination) and it locally flattens out above its low hardness of about 30 to 70 Shore A at the valve seat sealing ring. Thereby, high surface compression locally arises which represents the decisive criteria of a locally effective sealing bridging of local irregularities of both sealing surfaces or foreign objects locally present in the sealing zone. In the case of most of the so far proposed valve designs, the valve sealing ring zone is thin-walled and generally or as a whole a little stiffer. Thereby, the irregularities and foreign objects lead to a general deformation of the sealing ring zone and not to a local bridging and encapsulation, hence, the sealing effect is reduced by local spacing or gab formation. Therefore, the valve according to the present invention seals in a more reproducible manner and in a better way under the influence of local surface defects and foreign objects present in the sealing zone.

6c. The design similar to a rolling bellows also has an influence on the linearity of the spring property of the axial shifting of the sealing ring. Starting from a certain axial minimum deflection, rolling bellows comprise a constantly continuing or even declining force at any further deflection. The minimum deflection is then reached when the bending stress condition does not change anymore, i.e. the rolling bellow has taken a similar constantly continuing form. The thereto required deflection axial path is by a genuine rolling bellows about 3 to 5 times higher than the strength of the rolling bellows. Through the prestressing or bias of the cap valves, such a path, may be impressed. This is not possible with prestressing-free designs due to the limited activation path of 0.8, because only ca. 0.4 mm remain from this path, which is already less than the present rolling bellows strength, for the axial prestressing or bias after having deducted the minimum sterilization slot and the addable up tolerances. The typical rolling-bellows property of limiting the axial force enables that the valves are designed such that the force path characteristic line approximately horizontally proceeds and therewith the tolerance sensitivity of the opening pressure and of the flow resistance may still be reduced one more time.

7. Through the prestressing or bias of the valve in the cap and the release of this prestressing or bias and other prestressing or bias in the second or activated position, the new valve may be prestressed with a clearly higher path than valves without cap and without prestressing or bias; therefore, more flexible spring membrane geometries, having flatter spring characteristic line, may be utilized in the second position and therewith leading, by same activation path irregularities, to smaller uncertainties of the opening pressure like the pressure drops and irregularities in pressure drops.

8. However, due to the fact that the cap conceptions, as explained supra, lead to an extensive decoupling of the valve from the actuator of the machine and moreover the geometrical tolerances will decrease by skillful component arrangement or lay out, the tolerances of the above-mentioned characteristic line values are further reduced.

9. Through the tolerance-low second, activated position in connection with the flatter valve spring characteristic line and the stronger prestressing or bias, a particularly safe remanent activation of the valve, after the removal of the disposable, is reached. The cap, which is frictionally retained in the activated position, does not actuate itself when an excess pressure of up to 0.6 bar develops or arises in the disposable. In practice, this pressure cannot occur under regular removal conditions as the gas compliance of the emptied or drained disposable does not permit the development of such pressure.

The wedge effect and the higher sealing compression are accompanied in certain embodiments according to the present invention by a higher self-cleaning effect of the valve during opening and closing, a particularly useful property, because, due to the wedged-shaped arrangement of the valve seat sealing ring, normal and tangential movement overlap during the lifting off of the valve there, whereby the tangential movement causes or brings forth the cleaning effect, however also, up to the lifting off of the valve, the here desired hysteresis effect (higher opening pressure) after a longer-lasting sealing time. The preferred conical valve sealing seat has, as already further indicated above, more favorable angle tolerance properties than a flat valve seat, as it comes closer to resemble a shape of ball scraper. In an ideal embodiment, the valve sealing seat may take the form of a ball scraper, which is impressed by exactly the radius that corresponds to a tolerance-limited pendulum inclination of the valve axis to the valve seat axis: In this case, the valve sealing ring requires only a minimum of general elastical deformation in order to adjust itself to the valve sealing seat ring. However, the dimensioning of the prestressing or bias relationships is more difficult, as the cone walls do not have any constant increase any further.

Attempts or experiments with air and different fluids have shown that the valve in certain embodiments according to the present invention, in the provided volumetric flow area, does not create any audible noises or measurable pressure vibrations. By radiography or X-ray photograph with continuous flow through of air, it was possible to observe a regular opening. It is associated therewith that the valve design in certain embodiments according to the present invention has only a slight tendency for clogging or loading through clinging particle, in particular with regard to clinging clotting blood, as no seal-remaining sections are left, in which the blood flow comes to a halt or stop. The conical design forms a flow channel which most continuously directs the specified geometrical course of inflow from inside-down to top-outside. The outcome of this is also a less flow loss of the flowing of the housing (due to less abrupt change of direction of flow) and an improved ventilation possibility of the main flow path (due to higher average flow velocity).

By very high volumetric flow outside of the specified areas, the interior arched capping of the cap acts, in certain embodiments according to the present invention, as movement stop for the valve retaining ring which is being lifted by the fluid. The flat movement stop is geometrically designed in a way that no possibilities of deadlock of the valve onto the cap arch may arise. With the arising typical barrier or sealing pressures up to about 1.5 bar and within the specified volumetric flow range from 0 to 600 ml/min, the valve opens by itself through bending movements, whereby the inner material portion of the valve is kept almost free of play between centering cone and stop end and the retaining ring is spaced in all spatial directions without touching or contact distance to cap and valve seat. With drop of sliding movements (e.g. by valves with re-locatable balls), the characteristic line is highly reproducible and almost hysteresis-free. By normal barrier or sealing pressures up to 2.5 bar, the sealing ring area of the valve continuously comes to sit more tightly to the sealing cone of the valve seat and reinforcing or intensifying the sealing effect. By extreme barrier or sealing pressures up to ca. 5 bar, the spring membrane area of the valve buckles to the inside and returns back into the correct initial position or state by pressure withdrawal. By normal and extreme barrier or sealing pressures, the centering protrusion in the center of the valve seat prevents an axial movement or shifting and an axial-radial misalignment of the valve position. In addition, it diminishes the flow space and, hence, contributes to consistent flow velocities.

By longer phases of higher volumetric flows, the valve relaxes, in certain embodiments according to the present invention, some millibar towards the decreasing flow resistance, a typical reaction of elastomeric material. Among or under these materials, the silicon rubber has a significant place due to especially lower relaxation. However due to the fact that also the cap relaxes, through the persisting residual axial force onto the cap, towards the valve seat base, a compensating effect takes place as this relaxation direction is consistent with the increasing prestressing or bias direction. In this way, the cap-valve design offers a particular lower relaxation of the pressure volumetric flow characteristic line through the compensating mounting arrangement. Throughout suitable series of tests or experiments, the geometrical configuration, in particular of the cone seat area of the cap, can be optimized, taking into consideration the component or element tolerance of disposable and machine, the treatment temperatures and times and the wear and tear operations of the machine, so that an optimal middle mutual compensation of the relaxations of valve and cap is determined and implemented.

The tightness of the equipped cassette disposable in the place where the valve is intended to be located at or in, has proven to be so unreliable that a closure sleeve (having the corresponding seal function), in particular at the substitute connector, can be omitted by series disposable, see here the reference numeral 41 in FIG. 1 of International Patent Publication No. WO 2010/121819 A1. This is accompanied by further simplification of the machine-sided actuator-sensor-coupling mechanism, which does not need to use a hub for the sealing activation of the closure sleeve anymore and at the same time performing more economically and more reliably.

DETAILED DESCRIPTION

The present invention shall be exemplary explained with reference to the appended drawings or illustrations, in which identical reference numerals refer to same or identical elements. In the partially strongly simplified figures, the following applies:

Figure 1A:
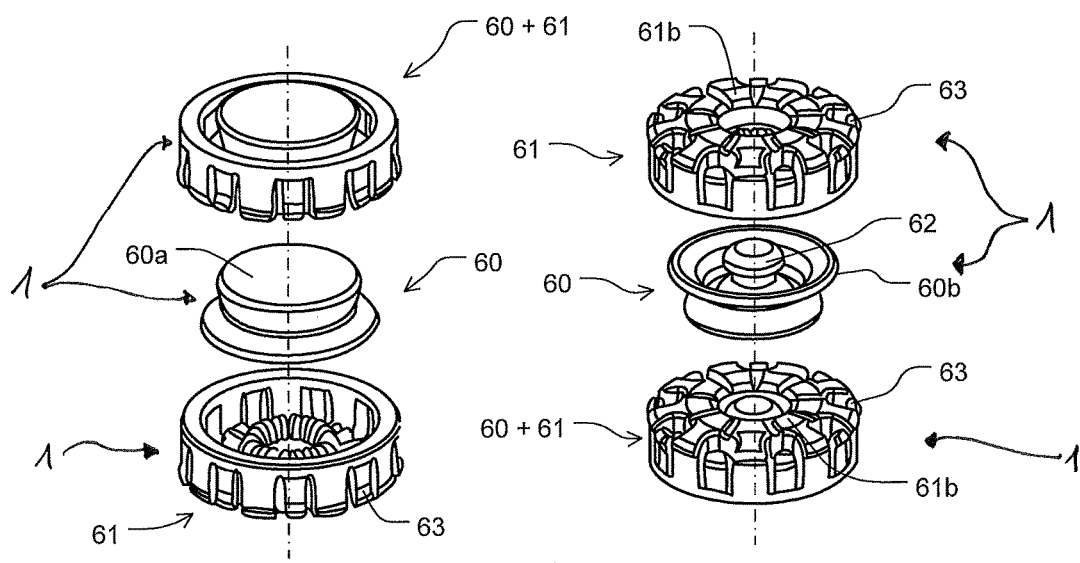
FIG. 1a to 1c show the valve arrangement according to the present invention in a first exemplary embodiment.
Figure 1B:
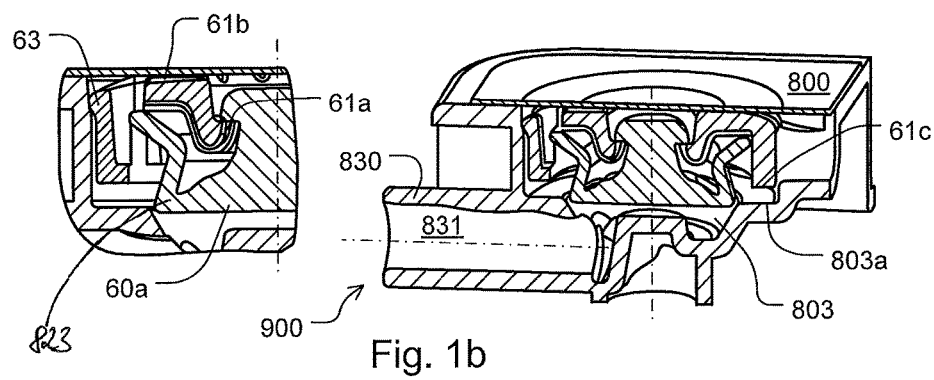
Figure 1C:
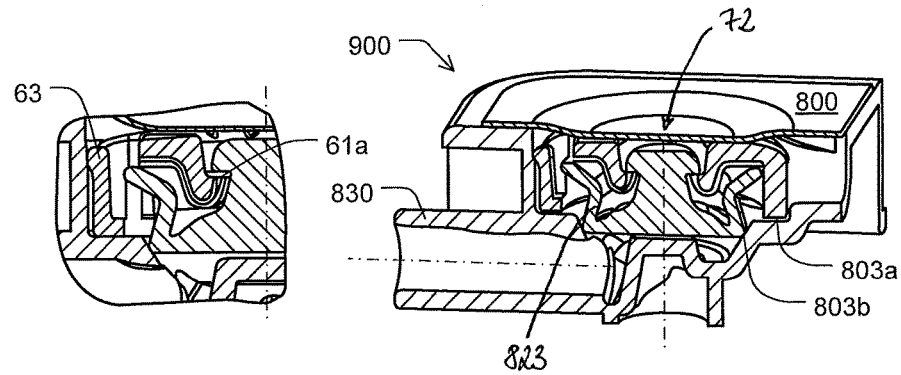

The FIG. 1a to 1c show the valve arrangement 1 in a first, exemplary embodiment.

The FIG. 1a to 1c show a valve arrangement 1 of a further, exemplary embodiment according to the present invention. This is a two-piece valve arrangement 1, which conically seals, having a valve component made of elastomer (preferably silicon rubber) and a cap component made of thermoplastic (preferably PP), which are inserted in a valve seat 803. Thereby, the FIG. 1a shows the valve arrangement 1 in an exploded view looked at from the bottom (left) or from the top (right), wherein the illustrated top or bottom, and the respectively centrally illustrated, components are again assembled on the bottom or top (with reference to the drawing sheet). The FIG. 1b shows the valve arrangement 1 in a so-called "pre-stressed" (expression shall be explained below) position, for example a first position during the mounting of the valve arrangement 1, and the FIG. 1c shows the valve arrangement 1 in a second position during the exemplary use of the valve arrangement 1 as a check valve. The illustrations of the FIG. 1b to 1c reproduced on the left, respectively, show the associated section enlargements to each illustration on the right.

The valve body 60 has here, exemplarily, the shape of a cup or a bowl with bellow-shaped envelope, flat to large extent, comparatively stiff valve tray 60a and with a central and stiff tension rod 62 fastened at the valve tray 60a. By the pre-assembly, the valve body 60 is snapped in by means of the tension rod 62 in a suitable, central snap-in opening of the cap 61.

Notwithstanding the arrangement of the valve body 60 in FIG. 1a to 1c, the valve body 60 may have the design of a vessel which is open at a front/end thereof, wherein a tension rod 62 extends towards the open front/end and, when appropriate, protrudes out of it.

The ring front/end 60b of the bellow envelope facing the valve tray 60a is radially positioned in the cap 61 under light prestressing or bias of e.g. about 0.1 mm and axially under preferably larger prestressing or bias of e.g. about 0.5 mm. Thereby the bellow is compressed accordingly and the axial prestressing or bias is maintained above the snapped-in, relatively stiff tension rod 62. The valve is hence centered in a prestressed, complete, free-of-play, radial manner and retains this property also by later activation of the cap 61 and by opening of the valve by means of flowing through of fluids. This axial prestressing or bias is denoted herein as prestressing or bias of the valve. This property or feature is only possible when using the cap 61 and it offers or conveys benefits or advantages. Hence, without prestressing or bias, the activation path would have to be selected so large such that it ensures in the present example a sterilization slot of about 0.2 mm in the first position, by taking into account all tolerances and disposable components including the disposable production. Further, the activation path would have to be selected so large such that it comprises, in the first position taking into account all tolerances of all components including the machine, an axial prestressing or bias of the sealing ring of the elastomer component against the (here conical) sealing ring of the valve seat which leads to the desired safe fluid tightness up to the desired opening pressure. By a desired opening pressure of e.g. 180 mbar, an exemplary axial prestress force of about 1 N is required. In the case that the safely realizable activation path of the cap is e.g. 0.8 mm (and the therewith associated gross activation path, retained on machine side, is ca. 1.4 mm) and the tolerances of the pre-assembled or pre-mounted disposable are, summed up together, 0.2 mm, then there will still be 0.4 mm for the actual axial prestressing or bias of the valve in the second position. The middle spring rate of the axial flexibility of the valve is therefore 2.5 N/mm or 45 mbar/0.1 mm. By an uncertainty of the dimensions of 0.2 mm, this will lead to an uncertainty of the opening pressure of 90 mbar, i.e. of 50% of the set value. By an increase of the fluid flow rate of e.g. 600 ml/min, this would, for example, result in a pressure drop of 600 mbar.

By means of the prestressing or bias described supra and a warping or deformation of e.g. 0.4 mm, one advantageously achieves that, by the same path and tolerance relationships as mentioned before, the tension rod 62 in the position of the valve shown in FIG. 1b will just safely axially lift up from a ring front end 61a of the cap 61 which is arranged at the tension rod 62. So now the result is: 0.4 mm+0.4 mm=0.8 mm for the actual axial prestressing or bias of the valve. The middle spring rate of the valve 1 should therefore be now only 1.25 N/mm or 22.5 mbar/0.1 mm in order for the desired opening pressure to again be 180 mbar; this time however with the halved uncertainty of 45 mbar, i.e. of only 25% of the set value. Due to the fact that the spring characteristic line has become flatter, a flatter pressure drop volumetric flow characteristic line is obtained in order to obtain, for example by a flow rate of 600 ml/min, a pressure drop of about 450 mbar. This low pressure drop on the other hand positively acts on the accuracy of the characteristic line and has in addition further positive properties: The pumps in the cassette 900 and in the machine (not shown) may, for example by using the valve according to the present invention, be designed, with corresponding lower pressure, as an inlet check valve of the dialysate. The inlet check valve for the venous luer addition may be designed to a smaller opening pressure due to the larger reproducibility of the opening pressure, whereby the operating person requires less efforts for pressing the content of a medication via a syringe into the blood circuit. Due to the fact that this valve may also be used for the arterial blood return at the completion of treatment, along with the flow velocities, the pressure drops and shear rates decrease as well, whereby the hemolysis is reduced accordingly.

The cap 61, optionally made of the relatively stiff material PP (bending module of elasticity ca. 1750 N/mm), has again the task of receiving, in a free-of play prestressed manner, the preferably elastomeric valve body 60, which is preferably made of the relatively flexible material of silicon rubber (bending module of elasticity ca. 15 N/mm), to keep it with lower axial tolerance of e.g. +/−0.1 mm in the first position and to transfer it with likewise lower tolerance in the second position, in which a ring surface 61c of the cap 61 facing the film and ring surface 803a of the valve seat 803 touch each other. Thereby, the clearly larger tolerance of the activation path and the associated activation axial force, brought forward from the machine through the purely optionally provided actuator-sensor-matt 950 via a therethrough effecting actuator 951 in the example of the figures (see FIG. 3f), are kept distant and decoupled from the valve, which is not possible to achieve without the stiff cap 61 positioned between film 800 and valve body 60. Also in the herein represented embodiment of the cap 61, the latter is flush mounted or fitted or built in, in a simple manner and with its ring front/end surface 61b facing the film, with the film plane of the channel edges of the cassette 900. The cap 61 has radially-extending, radially-protruding or radially-rebounded tongues or pins 63. They are accountable for providing the defined and safe frictional-closure retaining of the valve arrangement 1 in the valve seat 803. The spring-tongue or pin functionality shall be described in details with reference to FIG. 3a to 3d. The cap 61 is, on the other hand, preferably equipped on all sides with numerous drainage and through openings structures, which ensure the safe gas sterilization and ventilation as well as guarantee the pressure-drop-free passage (the amount of pressure drop without a valve is lower than ca. 10 mbar at 600 ml/min).

The valve seat 803 is a part of the cassette 900, which again comprises a hard body 830 having a connector-sided space 831.

The prestressing or bias of the valve body 60 results in the example of FIG. 1b through the support of the tension rod 62 against the ring surface 61a of the cap 61. In the position shown in FIG. 1c, the tension rod 62 is however not supported onto the ring surface 61a anymore. A tension of the valve body 60 arises by the involvement of the conical ring section 803b, which may comply with the sealing zone 826 of the FIG. 3d.

Figure 2A:
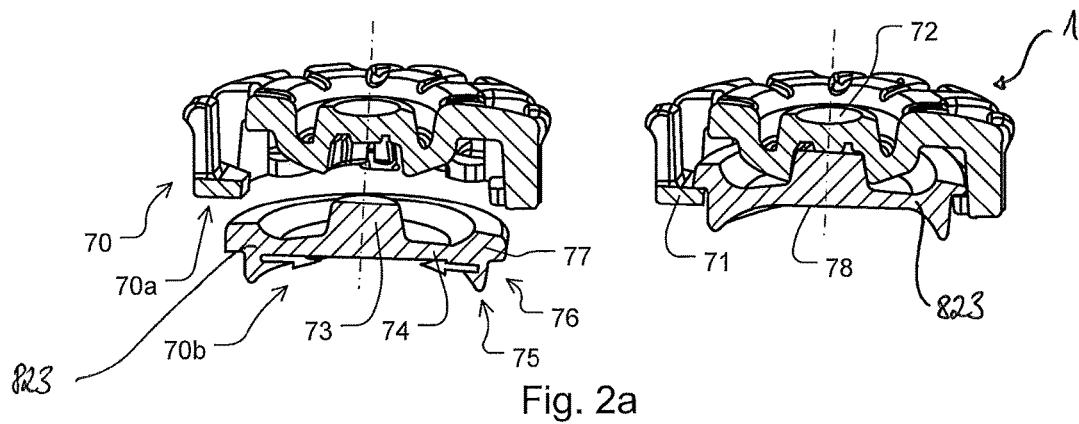
FIG. 2a to 2d show a further design of a two-piece prestressed valve with elastomeric valve body and thermoplastic cap and FIG. 3a to 3d show a further embodiment of the medical functional device according to the present invention, here purely exemplary a blood cassette, having a valve arrangement in an exploded view.
Figure 2B:
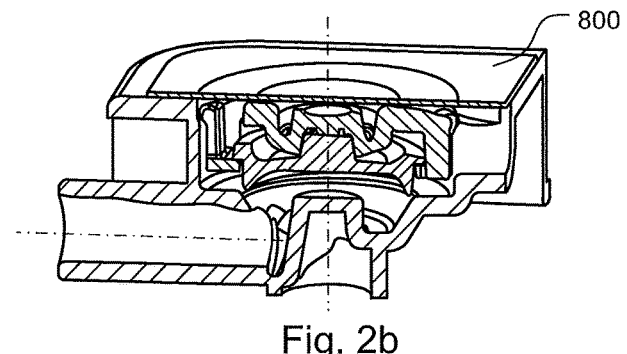
Figure 2C:
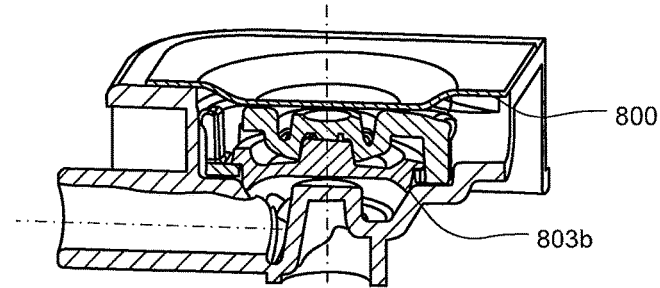
Figure 2D:
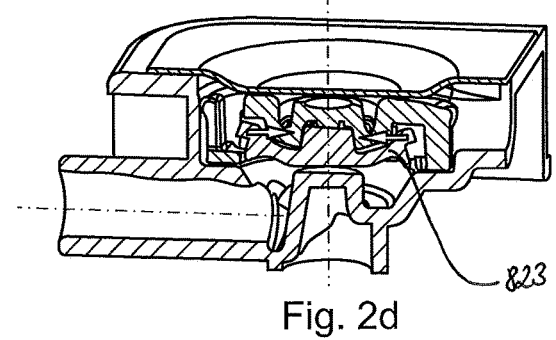

The FIG. 2a to 2d show a further design of a two-piece, prestressed valve having an elastomeric valve body and a thermoplastic cap, which are inserted in a valve seat. The FIG. 2a shows the valve arrangement 1 in an exploded view (left) and assembled (right). The FIG. 2b shows the valve arrangement in prestressed, first position, the FIG. 2c shows it in the second position, however without flow, and also the FIG. 2d shows it in the second position, however with or during maximum flow.

The cap 70 retains to a large extent its design, which is known from the aforementioned figures, but additionally comprises now, at the bottom ring front/end 70a, retaining protrusions or retaining noses 71, which are protruding, radially to the inside. The exemplary cap 70 of the FIG. 2a to 2d is designed to be produced by a multiple open-close injection molding with respectively optional, central hot channel injections and very economically.

The cap 70 comprises a central actuator working surface or contact surface 72, on which an actuator 950 can impact through the film 800.

The valve body 70b comprises a centrally conical mandrel 73, which is free-of-play received in the corresponding cone of the cap 70. A connecting membrane 74 extends between mandrel 73 and a retaining sealing ring 75-76-77.

The valve body 70b comprises, in the non-equipped state, a slight warping of a connection membrane or membrane 78, which is arranged centrally, towards the bottom, (with reference to the illustration in FIG. 2a), or facing away from the film. By the pre-assembly of the valve body 70b in the cap 70 through snapping in the support flange 76 of the retaining sealing ring 75-76-77 until its toothing or interlocking with the retaining noses or lugs 71 of the cap 70, such that the support flange 76 comes to lie on the retaining nose or lug 71, this warping will be already neutralized or the membrane 78 will already be so elastically deformed such that a slight warping in the opposite direction, i.e. to the top, see FIG. 2b, is formed. The warping in the opposite direction is reinforced or intensified by the activation, i.e. by the transfer into the second position, see FIG. 2c, and once again by flow through of treatment fluids, see FIG. 2d.

The retaining seal ring 75-76-77 is, in relation to membrane 78, configured in a compact or thick-walled manner. By the axial shifting of the retaining sealing ring 75-76-77, relative to the mandrel 73, a bending stress takes place, on the one hand side, in the membrane 78 which constantly has the effect of warping or deforming the retaining sealing ring 75-76-77 again to the bottom in the originally intended technical injection molding design. On the other hand side, also a hoop tension takes place by the axial shifting of the retaining sealing ring 75-76-77. This hoop tension tries or strives to warp or deform the retaining sealing ring 75-76-77 back to its initial diameter. Thereby the retaining sealing ring 75-76-77 has the largest diameter in the situation by which the membrane 78 is substantially flatly warped and therefore applies compression stress outwardly onto the retaining sealing ring 75-76-77. Once this neutral point is exceeded, the compression pressure decreases again and the retaining-sealing-ring 75-76-77 adds or steers an axial force component which tries to move it or shift it in the opposite position (in direction of the valve opening). This axial force component overlaps with the constantly increasing bending stress in the membrane 78 and leads to a decrease of the spring rate of the valve opening characteristic. Only through the prestress in the cap 70, it is possible to reach sufficiently high paths, by the actual prestress of the valve body 70b in the second position, under which this re-arching effect allows for or enables further flattening of the characteristic line.

The retaining sealing ring 75-76-77 can be a peripheral, radial section which comprises two diameters which are different from each other with a step disposed between them, and which closes, in a section radial thereof, the valve body (i.e. the radial edge).

The FIG. 2a to 2c show thereby a valve arrangement 1 in the form of a mandrel disc in a cap or of an inserted mandrel of the valve body in a cone of the cap which is two-piece, made of elastomer/thermoplastic and seals conically.

The prestressing or bias of the valve body 70b results in the example of FIG. 2b through the support of the valve body 70b against the retaining noses or lugs 71 of the snap in cap 70. In the position shown in FIG. 2c, the valve body 70b is however not supported onto the retaining noses 71 anymore. A tension of the valve body 70b arises by the involvement of the conical ring section 803b, which may comply with the sealing zone 826 of the FIG. 3d.

The FIG. 3a to 3d show a further embodiment of the medical functional device according to the present invention, in this case, purely exemplarily, a blood cassette 900 having a valve arrangement 1. They show in an overall view the parts or elements of the valve arrangement 1 in a perspectively exploded illustration in half-section. The cassette assembly consists of a half-open treatment cassette 900 or its valve seat 803 which is open to the top, preferably made of PP or other thermoplastic injection molding material, e.g., polyvinyl chloride (in short: PVC) or polycarbonate (in short: PC) and a covering film 800, see FIG. 3a, flushed on the channel edge closing thereby the cassette 900 being however sufficiently flexible, preferably made of PP-TPE laminated or multi-layered extrudates ("TPE" stands for thermoplastic elastomer) or of other flexible extrudate material like e.g. soft PVC or thermoplastic polyurethane (in short: TPU).

The film 800 has a thickness of e.g. 0.24 mm and it is flush at the edge of the peripheral film bar 814 in a welded, glued or compressed manner. The film is preferably flatly arranged in the initial state, i.e. in the first position, so that it can possibly be attached or affixed to the cassette; it can advantageously be dented to the top (i.e. away from the cassette 900) for a particularly little or no stretching stress of the film 800, such that only one dent takes place by the shifting or movement required for the activation. By the flat film arrangement, a stretching of the film of less than 2% is a result of the low activation hub of e.g. 0.8 mm. The cost-effective film type, used here, having little elastomeric proportions can be stretched without the risk of destruction, wherein the film 800 initially takes in a force of ca. maximum 20 N by the valve activation through said stretching. This force is to be at first additionally applied, which reduces to almost zero in the course of treatment through plastic deformation of the film.

Figure 3A:
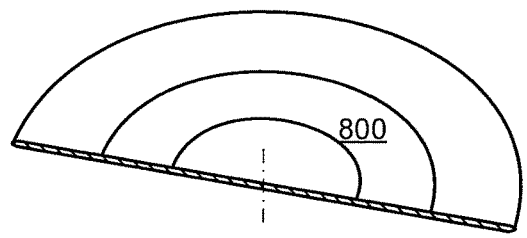
Figure 3B:
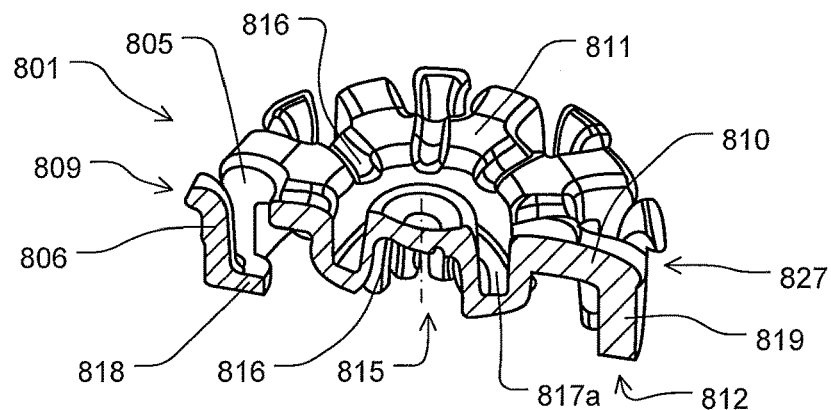
Figure 3C:
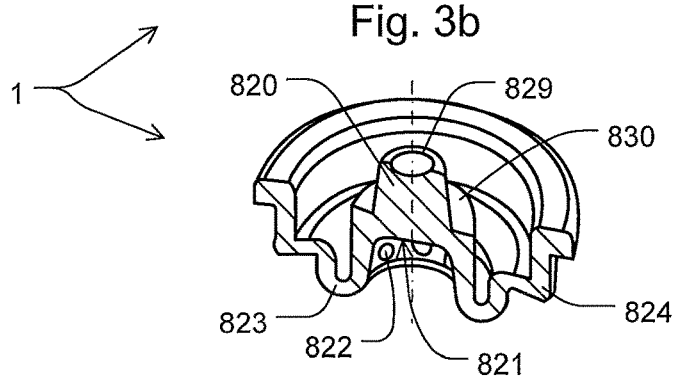
Figure 3D:
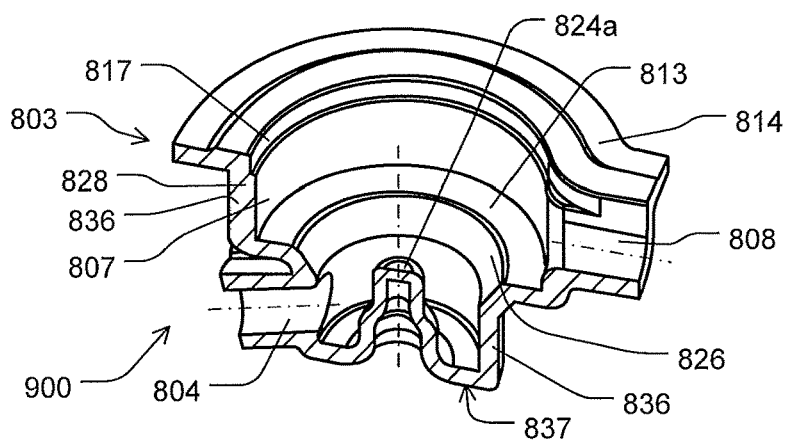

The valve seat 803 of FIG. 3d is exemplary geometrically configured or designed so that it does not comprise any undercuts as an injection molding for the demolding process. Due to the fact that the function of the valve in the treatment cassette 900 relates always to fluids which arrive from hose lines and should flow into the cassette 900, cassette 900 anyhow needs a cylindrical pipe arrangement 804 at the relevant points or places. The cylindrical pipe arrangement 804 opens via a hole into the channel and chamber arrangement of the cassette 900 (i.e. herein into the lower area of the valve seat 803). Insofar, almost no additional costs shall arise for integrating the check valve-valve seat of the illustrated design in cassette 900.

The valve seat 803 contains at least one outgoing fluid channel 808.

The valve seat 803 in fixing or activation direction is particularly designed in a stiff way through cylindrical, almost vertical cylinder walls 836 and through a wide valve seat support front/end 837, which can be a peripheral surface and which can be disposed vertically or substantially vertically at or on the cylinder walls 836 or can merge into those.

The—only preferably cylindrical—pipe arrangement 804 can open into the cylindrical walls 836.

The outgoing fluid channel 808 preferably goes out above the cylindrical walls 836.

The valve arrangement 1 consists of the cap 801 (preferably made of PP or made of other relatively stiff thermoplastic injection molding material like PC or hard PVC), see FIG. 3b, and the valve body 802, see FIG. 3c (preferably made of LSR (Liquid Silicon Rubber), a cost-effective mass of elastomer having sufficient low compression set, good resistance to sterilization and good hemo-compatibility.

The cap 801 has the shape of an arch having several openings or through-openings 805 which are radially to the outside and axially to the top open. In those openings or through-openings, snap-in tongues or pins 806 are arranged. They can radially bend to the inside, for example, with low force of ca. 1 N per 0.2 mm radial deflection of the points or peaks of the snap in tongues or pins 806. The snap-in tongues or pins 806 close the openings or through-openings only partially, e.g. to ca. 30%.

In the preferred embodiment, the number of the openings or through-openings 805 and the number of snap-in tongues or pins 806 is preferably uneven, respectively, because uneven division increases the exactness of centering of the cap 801 in the valve seat 803 (two two-dimensionally centering openings or through-openings 805 always face a snap-in tongue or pin 806 in those exemplary embodiments or the latter is neighbored by each of them while retaining a split or slot). The number of openings or through-openings or snap-in tongues or pins 806 is preferably 9 and can be advantageously within the range of 7 to 11 by a valve seat outer diameter of 33 mm.

Due to the relatively large number of openings or through-openings 805 or snap-in tongues or pins 806, it is possible to mount the valve arrangement 1 in the valve seat 803 without specified or determined orientation of rotation. Even when preferably vertical or substantially vertical cylindrical walls, herein denoted as cap reception valve seat cylindrical walls 807 and 817, are interrupted at one to three points through outgoing fluid channels, the remaining wall segments of these cylindrical walls or of the valve seat 803 are sufficient enough to sufficiently center or align the cap 801, to maintain it in the desired positions and to achieve throughout the openings or through-openings 805 sufficiently low flow resistance for the treatment fluid.

With maximum flow of about 600 ml/min, the mere flow resistances of the cap 801 in the mounted and activated state are, e.g., at ca. 20 mbar and comprise therefore only ca. 4 to 5% of the total flow resistance with mounted flowed-in valve 1.

The cap 801 is preferably designed to be cost-effectively produced in an open-close injection molding without a slide and with high number of cavities.

The cap 801 comprises a peripheral, preferably sharp edge, denoted with reference numerals 809 and 827, which is on the same level of the preferably with a U-shaped support arch 810 being open to the bottom which grants or reinforces stability to the cap 801, and the bendable or flexible snap-in tongues or pins 806 and thus building the separation plane of the injection molding. Due to the fact that by injection molding elements or components (above all when they are produced by means of multi-cavity molding) edges and mismatch in mold always occur in the main separation plane, a virtue is made out of necessity herein, in that the sharp angle of the edge and the systematical and radial mismatch in mold, included in the construction in the form of the edge or angle, are deliberately planned or intended to be the functional element for the valve function (elaboration further below).

An upper surface or plane, denoted herein also as upper cap front/end 811, forms the highest section or part of the vaulted or arched construction, which includes support arches 810, and represent through the film 800 the mechanical interface for the introduction or initiation of activation force, activation path and support force by the actuator-sensor-unit (abbreviated: ASE) of the machine. The upper surface or plane represents through preferably radial structuring grooves 816 uninterrupted, preferably flat ring front/ends, whose diameter can be in the range of 6.5 to 8.5 mm. Thereby, the diameter and the size or dimension of the ring front/end, being the effecting contact surface for an actuator 951 (see FIG. 3f) during the activation of the valve, are within a range which is advantageous for providing the activation hump (not illustrated) of the actuator-sensor-unit with enough transition area for force and path, however to be at the same time distant enough from the maximum seat diameter of 13 mm. In this way, on the one hand side, the stretching of the film 800 by the activation of the valve is limited and, on the other hand side, the activation force which is to be transferred and, solely expended for the stretching of the film 800 is minimized.

A surface or plane closing or covering the cap 801 to the bottom, herein also referred to as lower cap ring front end 812, forms together with a preferably peripheral or closed support surface of the valve seat 803, for the lower snap-in ring front/end 812, a functional system for ensuring a short activation path and precise constant condition of the cap 801.

Both on the upper ring front end 811 and in the area of the cone reception or intake 815 (which receives a centering cone 820 of the valve body in the operating state), the cap 801 comprises, optionally, several structurings such as structuring grooves 816, notches and rebounds which are needed for the sterilization gases to sufficiently reach many surface parts of the cap 801, the valve body 802 and the cylinder walls 807 and 817 of the valve seat 803.

In order for the element or component to sustain a symmetrical and an unremarkable warpage, these outer and inner structurings are arranged in a concentrical and even or equal number, divided in relation with the number of the through openings 805/snap-in tongues or pins 806. Due to the fact that number of the latter is preferably an uneven number, one can see in each half-section illustration or drawing (or in each front section through the middle point of the cap 801), on the one side (right or left), a snap-in tongue or pin, an arch or a support tongue or pin or a section thereof, while this is not the case on the opposite side due to asymmetry. This illustration in section should however not lead to the misunderstanding/misinterpretation that at a certain point or place, structures or supports are missing or elements or components hang unsupported in midair. Rather, there is an even distribution of material contact and non-contact through surface and extent.

Not only the arch or vaulted structures 810 contribute to the stiffness of the cap 801, rather also preferably, radially outwardly provided vertical cylinder walls 819 and the preferably peripheral walls, which are steeply conical, inside and outside of the peripheral slot, herein referred to as cap centering groove 817*a*. One obtains a structure with relatively even wall thickness by high axial stiffness. An axial force of 60 N on the upper ring front/end 811 of the cap 801, by support on the lower ring front/end 812 of the cap 801, leads merely to a lowering of the preferably central cone reception 815 of about 0.04 mm.

The diameter of the cylinder wall 807 of the valve seat 803, at which the edge 809 of the cap 801 abuts, is definably designed as larger than the stiff outer diameter of the cap 801, at the edge 827 of the arch 810, and as larger than the stiff outer diameter of the cap 801 at the chamfered peripheral edge towards the lower ring front end 812. With such play-design, the cap 801 may be tilted to up to 6 degrees, without canting at both hard diameters against the hard cylinder wall 807. A tilting of the cap 801 of more than 3.4 degrees, are mechanically not realizable anyhow by the application/mounting.

The valve seat 803 optionally comprises a snap-in level or step 828, which is disposed in the path from the cylinder wall 836 to the snap-in reception valve seat cylinder wall 817. It represents a diameter tapering or diminution to the interior of the valve seat 803.

The valve body 802 has, optionally, a rolling-bellows form and encompasses, again optionally, the functional elements centering cone 820, which is preferably centrally arranged and ascends towards the cap 801 up to a front/end surface 829 or locks up thererwith, a support front/end 821, against which, in the second position, a centering stop mandrel or fold 824*a* of the valve seat 803 strikes or bends, at least one auxiliary centering hump 822, which, at least in the second position, touches the centering stop mandrel or fold 824*a*, and a spring membrane 823, which is provided in a form of a peripherally closed (i.e. exemplary circular) however open to the top (with regard to the illustration of the figures in the mounted state). The valve body comprises further a preferably peripheral support or retaining ring 825 protruding radially outwards, which can only protrude through the tips of the centering mandrel, and which is the section of the valve body 803 protruding furthest to the radial.

In a preferred embodiment, the build-in opening of the valve seat 803 has a largest diameter of 13 mm (at the point of the film layer).

The centering 820 is, as seen in FIG. 3*c*, in certain exemplary embodiments according to the present invention, a centrally arranged truncated cone. Its cone envelope surface serves preferably both as introduction chamfer into the associated centering cone area or the cone reception 815, by the assembly, as well as radial centering towards cap 801 with defined low residual clearance.

The stop front/end 821 is in specific exemplary embodiments according to the present invention centrally arranged and can form the bottom surface of the truncated cone of the centering cone 820. In connection with the centering stop mandrel or protrusion 824*a* of the valve seat 803, both an axial, low play-restricted restriction of the valve as well as a movement stop by extreme operating pressures—when using the valve as a check valve—in the reverse direction of the valve take place.

The optional, auxiliary centering humps 822 form, in certain exemplary embodiments according to the present invention, together with the often rounded, substantially cylindrical envelope surface of the centering stop mandrel or protrusion 824*a*, in an advantageous manner, a further, usually slightly play-restricted, radial centering arrangement. The latter may, e.g. by means of the assembly procedure, contribute (or be responsible for) so that a tilting of the valve in the valve seat 803 is prevented, at the same time however, that during the operation a possibly low effect or influence on the opening characteristic of the valve is exerted.

The springy connection membrane or spring membrane 823 may advantageously be similar to rolling bellows. It can be advantageous for the correct positioning or fitting of the sealing ring 824 in both operation states or positions: Due to the fact that it is bendable or flexible, axial prestressings or bias and axial operation prestressings or bias of the sealing ring 824 may build up against the sealing ring zone 826. Thereby, the spring membrane 823 may radially form a fluid-tight zone up to the sealing ring 824. Ultimately, the spring membrane 823 can hold also the support or retaining ring 825, under prestressing or bias, onto the retaining lug or support tongues or pins 818, and it can align the support or retaining ring 825 radially, during the mounting and during the operation position in an open flow direction.

As seen in the FIG. 3*a* to 3*d*, the cap 801 brings the valve body 802, already by the factory-made insertion of the valve body 802 in the cap 801, in an elastically prestressed position, namely as soon as the valve body 802 is engaged in the snap-in 801.

The prestressed force, achieved in this way, is preferably just under the pressure or the force dimensioned, by which the valve should open when used as intended.

The person having skill in the art, realizes already from FIG. 3*c* what FIG. 3*e* to 3*h* show in details, namely that the spring membrane 823 may act or effect as spring or resetting element, when the valve body 802 in FIG. 3*c* is engaged in the cap 801 in FIG. 3*b*. In case the valve body 802 is engaged in the cap 801, the valve body 802, prestressed by means of the spring membrane 823, retains or supports itself, on one hand side, with support ring 825 behind the support tongues or pins 818 and on the other hand side with the centering cone 820 in the cone reception 815. In this condition, the spring membrane 823 is elastically prestressed, because the valve body 802 is forced, due to the dimensioning of valve body 802 and cap 801 in the equipped state, into the elastically prestressed condition through form closure.

When the cap 801, together with the valve body 802 being engaged in it, is inserted in the valve seat 803 in FIG. 3*d* such that the snap-in tongues or pins 806 are disposed in the valve seat wall or in the cap reception valve seat cylinder wall 817, in this case, a slot, of width b, is found between the sealing surface or sealing ring zone 826 of the valve seat 803 and the sealing ring 824 of the valve body 802. Between the support tongues or pins 818 and the valve seat stop ring support 813 a further slot, of width a, is thus present. When both slots are present (i.e. both are open or detectable), then the first position, which is suitable for the gas sterilization according to the exemplary embodiment of the present invention, is present or achieved. The slot b may be smaller or narrower than the slot a.

Through at least one of an impression of path/a shifting or movement or a force larger than the prestressing force on the cap 801, which is effected by pressing an actuator 951 (directly or through actuator-sensor-matt 950) onto the film 800, the slot b can be closed when or in that the sealing ring 824 is tightening-pressed or sealing-pressed onto the sealing surface 826. Thereby, it is assumed or expected that the cassette 900 is mounted stationary and the cap 801, having the valve body 802, is movable/adjustable relative to the valve seat 803. If the slot b is closed, then the second position of the exemplary present embodiment is present or achieved.

The cap 801 having the valve body 802 inserted in, is, due to the through openings 805 of the cap 801, permeable to fluid such that the fluid coming from at least one of the side or from the top may penetrate through the cap.

The required impression of path/shifting or movement for opening and closing the valve is very small, e.g. only 0.8 mm, between closed and open position in the embodiment example according to FIG. 3a to 3d. That allows a very flat spring characteristic line of the spring membrane 823 in connection with the prestressing or bias. The desired sealing force with which the sealing ring 824 should be tightening-pressed onto the sealing surface 826, is thus already achieved with very small impression of path and slightly changes with an increasing impression of path. As soon as the sealing ring 824 pushes against the sealing surface 826 due to an impression of path, a sealing force, according to a jump function or a step function or a discontinuous function, is available abruptly or in a step-wise manner.

Figure 3E:
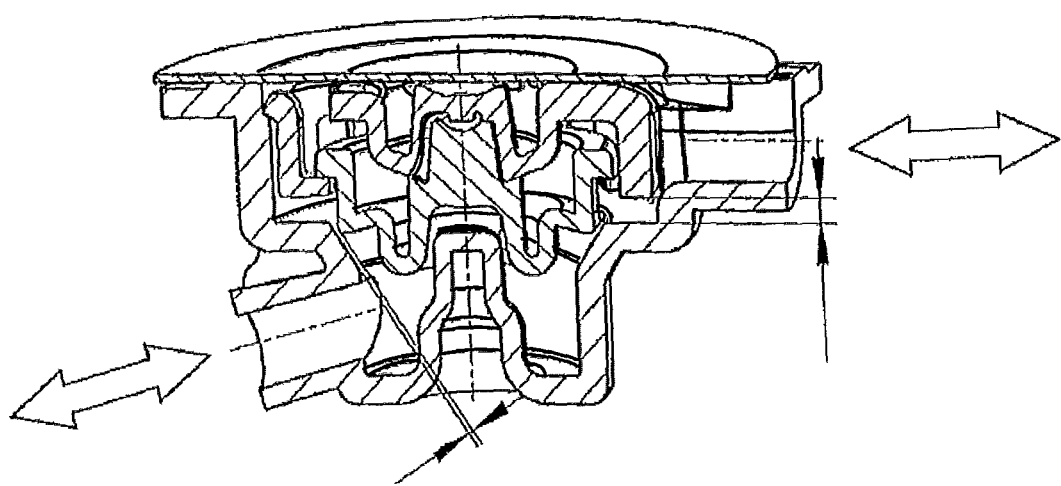
FIG. 3e to 3h show the embodiment of FIG. 3a to FIG. 3d in a jointed state in different valve positions.
Figure 3F:
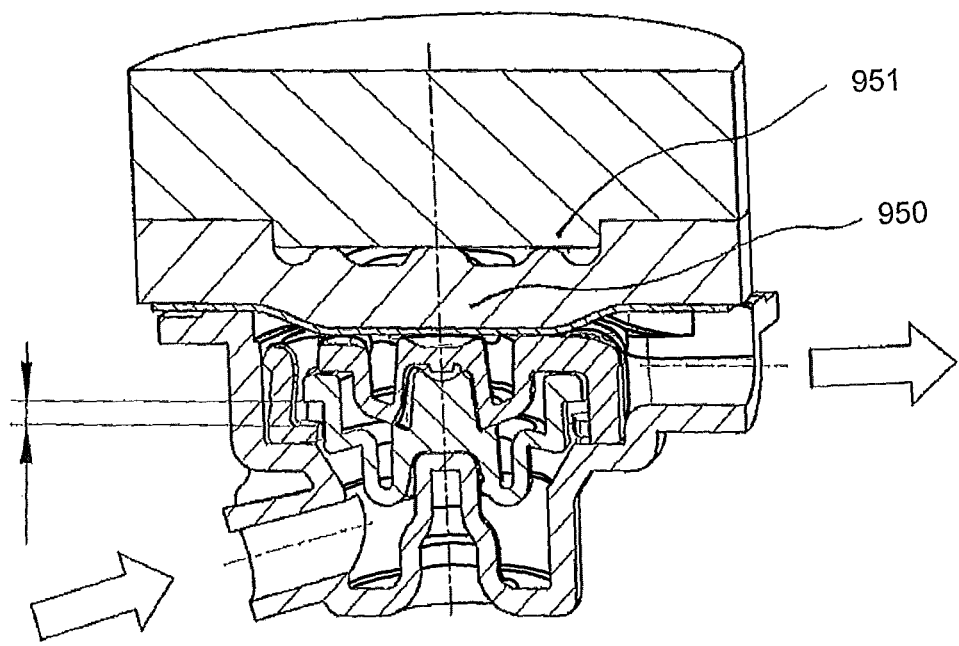
Figure 3G:
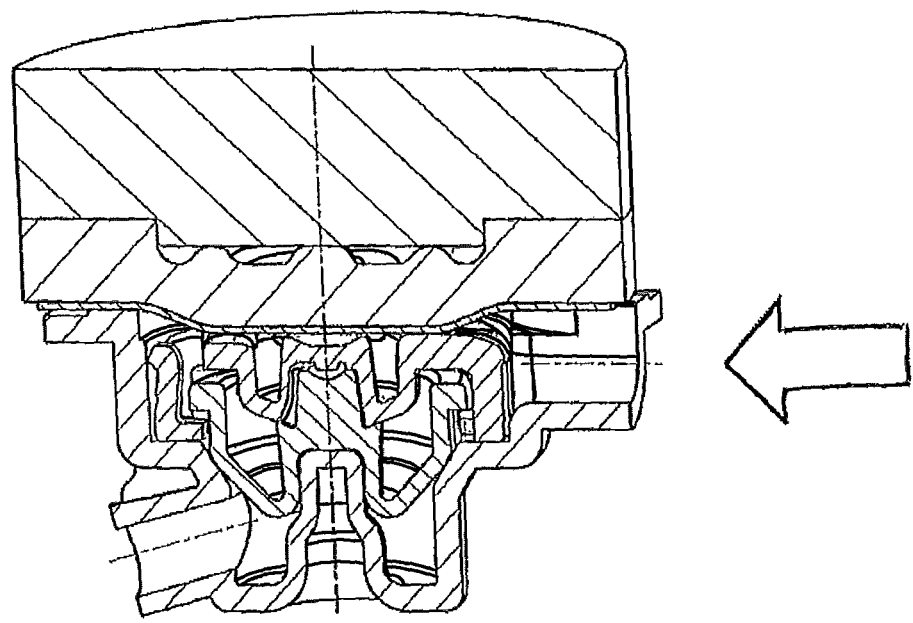
Figure 3H:
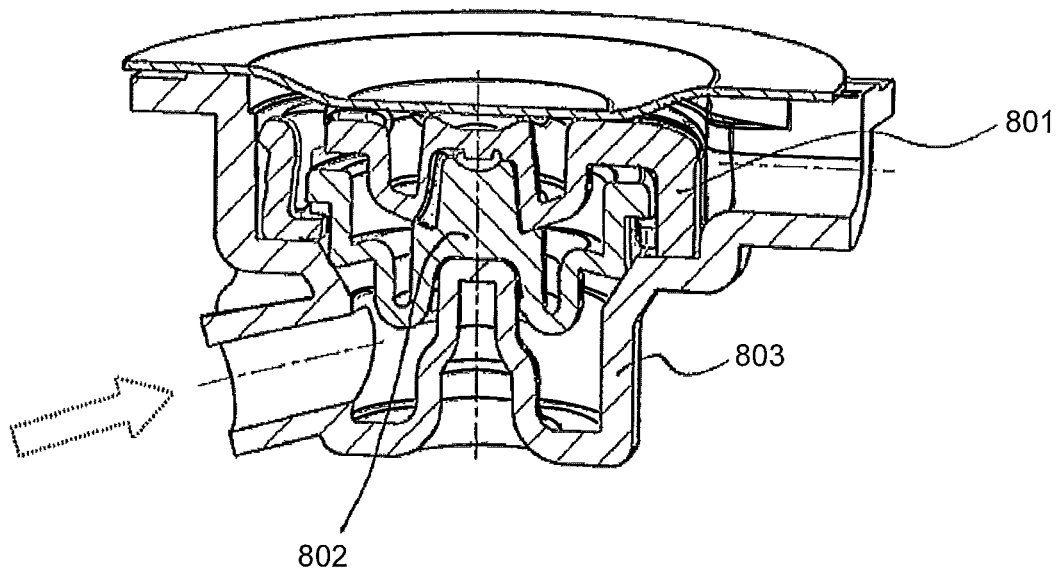

The FIG. 3e to 3h show the embodiment of FIG. 3a to 3d in a merged or assembled state in different valve positions. FIG. 3e shows them in a first, initial position prior to the closing of a machine door, FIG. 3f shows them in a second, activated position by closed machine door by maximum volumetric flow of the treatment fluid, FIG. 3g shows them in the second, activated position by maximum sealing pressure of the treatment fluid and FIG. 3h shows them in the activated, second position by open machine door, following the removal of the cassette 900 from the treatment device.

In the FIG. 3e to 3h, the big arrows indicate the volumetric flows; the small ones indicate slots which may be formed between the concerned elements or components.

The prestressing or bias of the valve body 802 results, in the example of FIG. 3a to 3h, from the fact that the valve body 802 is supported by means of its support or retention ring 825 onto the support tongues of pins 818 of the cap 801. Furthermore, its centering cone 820 sits closely at the cone reception 815. In the position shown in FIG. 3h, the valve body 802 is however not supported onto the support tongues or pins 802 anymore. A tension of the valve body 802 arises by the involvement of the sealing ring 824 of the valve body 802, which supports itself onto the sealing ring zone 826 of the valve seat 803.

LIST OF REFERENCE NUMERALS 1 valve arrangement, valve
60 valve body
60a valve tray
60b ring front/end surface of the valve body
61 cap
61a ring surface
61b ring front/end surface facing film
61c ring surface facing film
62 tension rod
63 pins
70 cap, embodied as snap-in cap
70a lower ring front/end
70b valve body
71 notches
72 actuator contact surface
73 conical mandrel
74 connecting membrane
75-76-77 support sealing ring
76 support flange of the support sealing ring
78 membrane
800 film
801 cap, embodied as snap-in cap
802 valve body
803 valve seat
803a ring surface
803b conical ring section
804 pipe assembly
805 openings or through openings
806 snap-in pin
807 cap reception valve seat cylinder wall
808 fluid channel
809 sharp edge
810 static supporting arch or vaulted structures
811 upper cap ring front
812 lower cap ring front
813 valve seat limit stop ring support
814 film bar
815 core reception
816 structuring grooves
817 cap reception valve seat cylinder
817a cap centering groove
818 support pin
819 vertical cylinder walls
820 centering cones
821 stop front end
822 auxiliary centering humps
823 spring element, embodied as spring membrane
824 sealing ring
824a—centering stop mandrel or fold
825 retaining ring
826 sealing ring zone
827 sharp edge
828 snap-in layer of the valve seat
829 front end surface
830 hard body
831 connector-sided space
836 cylinder wall
837 valve seat support front/end
900 cassette or medical functional device
950 actuator-sensor-mat
951 actuator

The invention claimed is:

1. A valve arrangement for a medical functional device, the valve arrangement comprising:
    a valve body connected to a cap,
    wherein the valve body and the cap are connected to each other such that the cap causes a prestressing or bias of the valve body in the cap,
    wherein the cap has an arched shape defining a plurality of openings or through-openings which extend radially and axially through the cap, and
    wherein the cap comprises snap-in tongues or pins arranged in the openings or through-openings which close the openings or through-openings only partially when said tongues or pins are radially bent inward.

2. The valve arrangement according to claim 1, wherein the valve body comprises a spring membrane that receives the prestressing or bias.

3. The valve arrangement according to claim 1, wherein the valve body is compressed by the cap.

4. The valve arrangement according to claim 1, wherein the valve arrangement is closed by means of an actuator of a blood treatment apparatus.

5. The valve arrangement according to claim 1, wherein the valve arrangement is configured as a check valve.

6. The valve arrangement according to claim 1, wherein both the valve body and the cap comprise drainage structures.

7. The valve arrangement according to claim 1,
wherein the valve body is positioned in the cap radially under a first prestressing or bias and axially under a second prestressing or bias, and
wherein the second prestressing or bias is larger than the first prestressing or bias.

8. The valve arrangement according to claim 1,
wherein the valve body is configured as a container or cup comprising a valve tray and a tension rod which is centrally fastened to the valve tray, and
wherein the tension rod connects the valve body with the cap so that the tension rod is engaged in a snap-in opening of the cap.

9. The valve arrangement according to claim 1, wherein the cap further comprises radially-extending tongues or pins or axially-extending and radially-deformable tongues or pins.

10. The valve arrangement according to claim 8, wherein the tension rod and the valve tray are sufficiently stiff so that the tension rod maintains a contact-free distance to other sections in at least one position of the valve arrangement in all spatial directions in the cap.

11. The valve arrangement according to claim 1, wherein the number of openings or through-openings and snap-in tongues or pins is uneven, respectively.

12. The valve arrangement according to claim 1, wherein the cap further comprises a closed or peripheral edge located at the level of the snap-in tongues or pins, to build a main separation plane of an injection molding.

13. A medical functional device comprising a valve seat and the valve arrangement according to claim 1.

14. The functional device according to claim 13, wherein the device comprises a blood cassette, a cassette, a blood tube or an infusion tube.

15. The functional device according to claim 14, wherein the blood cassette comprises a hard body and a film covering the hard body or parts thereof,
wherein the valve seat is provided in the hard body, and
wherein the valve arrangement is actuated or operated by pressure on the film or by moving or shifting an actuator of a blood treatment apparatus towards the film.

16. The functional device according to claim 15, wherein a film-sided surface of the valve arrangement does not project beyond a plane defined by the film of the blood cassette.

17. The functional device according to claim 14, wherein a snap-in position or step or a step-like or stacked diameter restriction is located within a cylinder-shaped section of the valve seat of the cassette, in an area in which a closed or peripheral section of the valve body lies in the valve seat.

18. The functional device according to claim 13,
wherein the valve body or the cap seals against the valve seat in at least one position, and wherein a sealing area of the valve seat is configured in a conical, cylindrical or flat closed or peripheral manner.

* * * * *